(12) United States Patent
Sugimura

(10) Patent No.: US 8,101,578 B2
(45) Date of Patent: Jan. 24, 2012

(54) AMYLOID [β] BETA FIBRILLOGENESIS-INHIBITING PEPTIDE

(75) Inventor: Kazuhisa Sugimura, Kagoshima (JP)

(73) Assignee: Kagoshima University, Kagoshima (JP)

( * ) Notice: Subject to any disclaimer, the term of this patent is extended or adjusted under 35 U.S.C. 154(b) by 488 days.

(21) Appl. No.: 12/298,672

(22) PCT Filed: Apr. 24, 2007

(86) PCT No.: PCT/JP2007/059350
§ 371 (c)(1),
(2), (4) Date: Oct. 27, 2008

(87) PCT Pub. No.: WO2007/126111
PCT Pub. Date: Nov. 8, 2007

(65) Prior Publication Data
US 2009/0088386 A1  Apr. 2, 2009

(30) Foreign Application Priority Data
Apr. 28, 2006 (JP) ................. 2006-125769

(51) Int. Cl.
*A61K 38/08* (2006.01)
*A61K 38/16* (2006.01)
*C07K 7/06* (2006.01)
*C07K 14/00* (2006.01)

(52) U.S. Cl. ........... 514/21.4; 514/17.8; 514/21.6; 530/326; 530/328

(58) Field of Classification Search ............ None
See application file for complete search history.

(56) References Cited

U.S. PATENT DOCUMENTS

| 5,854,204 A | 12/1998 | Findeis et al. |
| 6,462,171 B1 | 10/2002 | Soto-Jara et al. |
| 2005/0009749 A1 | 1/2005 | Ahn Jo et al. |
| 2006/0036073 A1 | 2/2006 | Windisch |
| 2008/0131422 A1 | 6/2008 | Sugimura et al. |

FOREIGN PATENT DOCUMENTS

| WO | WO 94/13798 | 6/1994 |
| WO | WO 96/11948 | 4/1996 |
| WO | WO 96/39834 | 12/1996 |
| WO | WO 98/30229 | 7/1998 |
| WO | WO 03/063760 A3 | 8/2003 |
| WO | WO 03/082906 | 10/2003 |
| WO | WO 03/089460 A1 | 10/2003 |
| WO | WO 2004/013172 A3 | 2/2004 |
| WO | WO 2004/096845 | 11/2004 |
| WO | WO 2005/066337 A2 | 7/2005 |

OTHER PUBLICATIONS

LeVine. The Challenge of Inhibiting A-Beta Polymerization. Current Medicinal Chemistry. 2002, vol. 9, No. 11, pp. 1121-1133.*
Office Action German Official File No. 11 2007 001 030.4-43 dated Oct. 18, 2010.
Takahiro Fukumoto et al., "Peptide mimics of the CTLA4-binding domain stimulate T-cell proliferation", Nature Biotechnology, vol. 16, Mar. 1998, pp. 267-270.
Annual Meeting for the year 2006, The Japanese Biochemical Society, Kyusyu Branch Program & Lecture abstracts, May 20, 2006 pp. 21 & 39.

* cited by examiner

*Primary Examiner* — Jeffrey E Russel
(74) *Attorney, Agent, or Firm* — Stephen A. Bent; Foley & Lardner LLP

(57) ABSTRACT

The present invention provides a peptide which functions as a mimic peptide of an amyloid β peptide and is capable of inhibiting the fibrillogenesis of an amyloid β peptide. The present invention relates to: an 8- to 30-amino acid residue peptide comprising an amino acid sequence represented by the following formula (I):

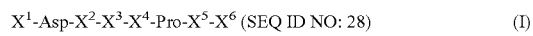

$$X^1\text{-Asp-}X^2\text{-}X^3\text{-}X^4\text{-Pro-}X^5\text{-}X^6 \text{ (SEQ ID NO: 28)} \quad (I)$$

wherein $X^1$ represents a branched chain amino acid, and $X^2$, $X^3$, $X^4$, $X^5$, and $X^6$ are the same or different and each represents an α-amino acid; a 9- to 30-amino acid residue peptide comprising an amino acid sequence represented by the following formula (III):

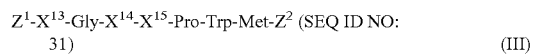

$$Z^1\text{-}X^{13}\text{-Gly-}X^{14}\text{-}X^{15}\text{-Pro-Trp-Met-}Z^2 \text{ (SEQ ID NO: 31)} \quad (III)$$

wherein $X^{13}$, $X^{14}$, and $X^{15}$ are the same or different and each represents an α-amino acid, $Z^1$ and $Z^2$ are the same or different and each represents cysteine or serine, and when $Z^1$ and $Z^2$ represent cysteine, they may be crosslinked; and a pharmaceutical composition and an amyloid β fibrillogenesis inhibitor comprising the peptide.

7 Claims, 9 Drawing Sheets

Fig. 5

| Phage clone name | Template antibody name | Amino acid sequence of peptide |
|---|---|---|
| 12 mer* | | |
| pepB6-L1 | B6 | G M L D I F A P I R H V |
| pepB6-L10 | B6 | T S P I L D V L T P P R |
| pepD1-L5, L9 | D1 | G S P F L D L L A P A A |
| pepD1-L6 | D1 | S S I I D I L L P P I Y |
| pepD1-L7 | D1 | S I L D I L S P R L A E |
| pepD1-L13 | D1 | G N T L L D T L V P L I |
| pepD1-L20 | D1 | N P L D F Y A P S I L P |
| C7C* | | |
| pepB7-C15 | B7 | C Y G T K P W M C |
| pepD1-C2, C13 | D1 | C F G T E P W M C |
| pepD1-C18 | D1 | C F G H E P W M C |
| pepD1-C3 | D1 | C Q G H L P W M C |
| pepD1-C11 | D1 | C F G H K P W M C |
| pepD1-C5, C7, C20 | D1 | C Y G T K P W M C |
| pepD1-C8 | D1 | C F G R L P W M C |
| pepD1-C10 | D1 | C F G S L P W M C |

Fig. 6

| Binding sequence name | Amino acid sequence |
|---|---|
| B6-L1 | GMLDIFAPIRHV |
| B7-C15G | CYGTKPWMCG |
| B7-S15 | SYGTKPWMSG |
| TAT | YGRKKRRQRRR |
| | |
| TAT-B6-L1 | biotin-YGRKKRRQRRRGMLDIFAPIRHV |
| B6-L1-TAT | biotin-GMLDIFAPIRHVYGRKKRRQRRR |
| TAT-B7-C15 | biotin-YGRKKRRQRRRCYGTKPWMCG |
| TAT-B7-S15 | biotin-YGRKKRRQRRRSYGTKPWMSG |

Anti-Aβ antibody/HRP-labeled anti-mouse antibody

AMYLOID [β] BETA FIBRILLOGENESIS-INHIBITING PEPTIDE

SEQUENCE LISTING

The instant application contains a Sequence Listing which has been submitted in ASCII format via EFS-Web and is hereby incorporated by reference in its entirety. Said ASCII copy, created on Jul. 29, 2011, is named 81356309.txt and is 18,843 bytes in size.

TECHNICAL FIELD

The present invention relates to an amyloid β fibrillogenesis-inhibiting peptide which is useful as a preventive or therapeutic agent for Alzheimer's disease.

BACKGROUND ART

With increases in aging population, the development of pharmaceuticals effective for the treatment of senile dementia has been demanded strongly in recent years. Alzheimer's disease, which is a typical disease of senile dementia, is a neurodegenerative disease characterized by brain shrinkage, deposits of senile plaques, and neurofibrillary changes. This disease develops when insolubilized molecules attributed to a change of forms of amyloid β peptides and following fibrillogenesis are deposited on neuronal cells such that neuronal cell death is induced by their toxicity.

Amyloid β peptides (Aβ) are degradation products generated by cleavage with β secretase, etc., from neuronal amyloid precursor proteins, and these degradation products are found in 2 forms, Aβ1-40 and Aβ1-42. It has been reported that Aβ1-42 is more likely to aggregate and more correlated to disease and neurotoxicity.

If a change of forms of amyloid β peptides and fibrillogenesis thereof can be inhibited, the development of Alzheimer's disease can be prevented.

The pamphlet of WO 2005/105998 describes that a single-chain antibody having an activity of specifically binding to Aβ1-42 such that the fibrillogenesis reaction thereof is inhibited is useful as a preventive or therapeutic agent for Alzheimer's disease.

However, antibodies are high-molecular-weight proteins and are therefore expensive. They also have problems such as complicated production and purification steps or a lack of stability.

Drugs having an effect of suppressing amyloid β peptide production, for example, a rhodanine derivative (JP Patent Publication (Kokai) No. 06-192091A (1994)), a benzimidazole derivative (U.S. Pat. No. 5,552,426), a vinpocetine derivative (pamphlet of WO 96/25161), and an aromatic amide derivative (pamphlet of WO 2004/014843), have been known as low-molecular-weight preventive or therapeutic agents for Alzheimer's disease.

DISCLOSURE OF THE INVENTION

An object of the present invention is to provide a peptide which functions as a mimic peptide of an amyloid β peptide and is capable of inhibiting the fibrillogenesis of an amyloid β peptide.

The present invention is summarized as follows:

(1) An 8- to 30-amino acid residue peptide comprising an amino acid sequence represented by the following formula (I):

$$X^1\text{-Asp-}X^2\text{-}X^3\text{-}X^4\text{-Pro-}X^5\text{-}X^6 \text{(SEQ ID NO: 28)} \quad (I)$$

wherein $X^1$ represents a branched chain amino acid, and $X^2$, $X^3$, $X^4$, $X^5$, and $X^6$ are the same or different and each represents an α-amino acid.

(2) The peptide according to (1), wherein in the formula (I), $X^2$ is a branched chain amino acid, hydroxyamino acid, aromatic amino acid, or aliphatic amino acid.

(3) The peptide according to (1) or (2), wherein in the formula (I), $X^3$ is an aromatic amino acid or branched chain amino acid.

(4) The peptide according to any of (1) to (3), wherein in the formula (I), $X^4$ is an aliphatic amino acid, hydroxyamino acid, or branched chain amino acid.

(5) The peptide according to any of (1) to (4), wherein in the formula (I), $X^5$ is a branched chain amino acid, imino acid, aliphatic amino acid, basic amino acid, or hydroxyamino acid.

(6) The peptide according to any of (1) to (5), wherein in the formula (I), $X^6$ is a basic amino acid, aliphatic amino acid, or branched chain amino acid.

(7) The peptide represented by the following formula (II):

$$X^7\text{-}X^8\text{-}X^9\text{-}X^{10}\text{-}X^1\text{-Asp-}X^2\text{-}X^3\text{-}X^4\text{-Pro-}X^5\text{-}X^6\text{-}X^{11}\text{-}X^{12}\text{-}Y^1 \text{ (SEQ ID NO: 29)} \quad (II)$$

wherein $X^1$, $X^2$, $X^3$, $X^4$, $X^5$, and $X^6$ are the same as the definitions in the formula (I) according to (1), $X^7, X^8, X^9, X^{10}$, $X^{11}$, and $X^{12}$ are the same or different and each represents an α-amino acid or single bond, and $Y^1$ represents OH or $NH_2$.

(8) The peptide according to (7), wherein in the formula (II), $X^7$ is a hydroxyamino acid or aliphatic amino acid.

(9) The peptide according to (7) or (8), wherein in the formula (II), $X^8$ is a hydroxyamino acid or amide amino acid.

(10) The peptide according to any of (7) to (9), wherein in the formula (II), $X^9$ is an aliphatic amino acid, imino acid, hydroxyamino acid, or amide amino acid.

(11) The peptide according to any of (7) to (10), wherein in the formula (II), $X^{10}$ is a sulfur-containing amino acid, branched chain amino acid, aromatic amino acid, or imino acid.

(12) The peptide according to any of (7) to (11), wherein in the formula (II), $X^{11}$ is a heterocyclic amino acid, aromatic amino acid, aliphatic amino acid, or branched chain amino acid.

(13) The peptide according to any of (7) to (12), wherein in the formula (II), $X^{12}$ is a branched chain amino acid, acidic amino acid, or imino acid.

(1) The peptide according to any of (1) to (13), wherein the peptide is a 19- to 30-amino acid residue peptide comprising the amino acid sequence represented by the formula (I) and a TAT sequence represented by the following formula:

(SEQ ID NO: 30)
Tyr-Gly-Arg-Lys-Lys-Arg-Arg-Gln-Arg-Arg-Arg.

(15) A 9- to 30 amino acid residue peptide comprising an amino acid sequence represented by the following formula (III):

$$Z^1\text{-}X^{13}\text{-Gly-}X^{14}\text{-}X^{15}\text{-Pro-Trp-Met-}Z^2 \text{ (SEQ ID NO: 31)} \quad (III)$$

wherein $X^{13}$, $X^{14}$, and $X^{15}$ are the same or different and each represents an α-amino acid, $Z^1$ and $Z^2$ are the same or different and each represents cysteine or serine, and when $Z^1$ and $Z^2$ represent cysteine, they may be crosslinked.

(16) The peptide according to (15), wherein in the formula (III), $X^{13}$ is an aromatic amino acid.

(17) The peptide according to (15) or (16), wherein in the formula (III), $X^{14}$ is a hydroxyamino acid.

(18) The peptide according to any of (15) to (17), wherein in the formula (III), $X^{15}$ is a basic amino acid.

(19) The peptide according to any of (15) to (18), wherein the peptide is a 20- to 30-amino acid residue peptide comprising the amino acid sequence represented by the formula (III) and a TAT sequence represented by the following formula:

(SEQ ID NO: 30)
Tyr-Gly-Arg-Lys-Lys-Arg-Arg-Gln-Arg-Arg-Arg.

(20) A pharmaceutical composition comprising the peptide according to any of (1) to (19).

(21) An amyloid 13 fibrillogenesis inhibitor comprising the peptide according to any of (1) to (19).

(22) The amyloid 13 fibrillogenesis inhibitor according to (21), wherein the inhibitor is a preventive or therapeutic agent for Alzheimer's disease.

(23) A method for screening an amyloid 13 fibrillogenesis-inhibiting peptide, characterized by searching, from peptides having no proven activity of inhibiting amyloid 13 fibrillogenesis, a peptide which binds to a single-chain antibody having an activity of specifically binding to an amyloid 13 peptide 1-42 such that the fibrillogenesis reaction thereof is inhibited, and has an activity of inhibiting amyloid 13 fibrillogenesis.

(24) An amyloid 13 fibrillogenesis-inhibiting peptide obtained by the screening method according to (23).

The peptide of the present invention is a peptide of 30 or less amino acid residues comprising an amino acid sequence represented by the formula (I) or (III) and is preferably an 8- to 20-amino acid residue peptide comprising an amino acid sequence represented by the formula (I) and a 9- to 20-amino acid residue peptide comprising an amino acid sequence represented by the formula (III).

In the formula (I), examples of the branched chain amino acid represented by $X^1$ include valine, leucine, and isoleucine.

In the formula (I), (II), or (III), examples of the α-amino acid represented by $X^2$, $X^3$, $X^4$, $X^5$, $X^6$, $X^7$, $X^8$, $X^9$, $X^{10}$, $X^{11}$, $X^{12}$, $X^{13}$, $X^{14}$, or $X^{15}$ include: aliphatic amino acids such as glycine and alanine; branched chain amino acids such as valine, leucine, and isoleucine; hydroxyamino acids such as serine and threonine; acidic amino acids such as aspartic acid and glutamic acid; amide amino acids such as asparagine and glutamine; basic amino acids such as lysine, hydroxylysine, and arginine; sulfur-containing amino acids such as cysteine, cystine, and methionine; aromatic amino acids such as phenylalanine and tyrosine; heterocyclic amino acids such as tryptophan and histidine; and imino acids such as proline and 4-hydroxyproline.

In the formulas (I) and (II), preferable examples of the α-amino acid represented by $X^2$ include branched chain amino acids, hydroxyamino acids, aromatic amino acids, and aliphatic amino acids, more preferably, valine, leucine, isoleucine, threonine, and phenylalanine; preferable examples of the α-amino acid represented by $X^3$ include aromatic amino acids and branched chain amino acids, more preferably, phenylalanine, leucine, and tyrosine; preferable examples of the α-amino acid represented by $X^4$ include aliphatic amino acids, hydroxyamino acids, and branched chain amino acids, more preferably, alanine, threonine, leucine, serine, and valine; preferable examples of the α-amino acid represented by $X^5$ include branched chain amino acids, imino acids, aliphatic amino acids, basic amino acids, and hydroxyamino acids, more preferably, leucine, isoleucine, proline, alanine, arginine, and serine; and preferable examples of the α-amino acid represented by $X^6$ include basic amino acids, aliphatic amino acids, and branched chain amino acids, more preferably, arginine, alanine, leucine, and isoleucine.

In the formula (II), preferable examples of the α-amino acid represented by $X^7$ include hydroxyamino acids and aliphatic amino acids, more preferably, threonine and glycine; preferable examples of the α-amino acid represented by $X^8$ include hydroxyamino acids and amide amino acids, more preferably, serine and asparagine; preferable examples of the α-amino acid represented by $X^9$ include aliphatic amino acids, imino acids, hydroxyamino acids, and amide amino acids, more preferably, glycine, proline, serine, threonine, and asparagine; preferable examples of the α-amino acid represented by $X^{10}$ include sulfur-containing amino acids, branched chain amino acids, aromatic amino acids, and imino acids, more preferably, methionine, leucine, isoleucine, phenylalanine, and proline; preferable examples of the α-amino acid represented by $X^{11}$ include heterocyclic amino acids, aromatic amino acids, aliphatic amino acids, and branched chain amino acids, more preferably, histidine, tyrosine, alanine, and leucine; and preferable examples of the α-amino acid represented by $X^{12}$ include branched chain amino acids, acidic amino acids, and imino acids, more preferably, valine, glutamic acid, and proline.

In the formula (III), preferable examples of the α-amino acid represented by $X^{13}$ include aromatic amino acids and amide amino acids, more preferably, tyrosine, phenylalanine, and glutamine, most preferably, tyrosine; preferable examples of the α-amino acid represented by $X^{14}$ include hydroxyamino acids, heterocyclic amino acids, and basic amino acids, more preferably, serine, threonine, histidine, and arginine, most preferably, threonine; and preferable examples of the α-amino acid represented by $X^{15}$ include basic amino acids, acidic amino acids, and branched chain amino acids, more preferably, lysine, glutamic acid, and leucine, most preferably, lysine.

The peptide of the present invention can also be synthesized chemically according to a method known in the art and can be synthesized, for example, using an automatic peptide synthesizer. The method described in R. B. Merrifield, Advances in Enzymology 32: 221-296 (1969) can be applied to a basic synthesis process thereof. In principle, this method involves covalently binding a carboxyl-terminal amino acid to a resin support and sequentially repeating removal of protecting groups of α-amino groups and condensation of protected amino acids such that a peptide chain is extended toward the amino terminus to obtain a peptide resin having the amino acid sequence of interest.

The condensation of each amino acid, the removal of a protecting group of each α-amino group, or the like is performed under almost the same conditions using the Boc or Fmoc method, and purification of intermediates is not performed. Therefore, this method generally requires no high skills for synthesis. In addition, this method is rapid and is very convenient for synthesizing various peptides. The protected peptide resin thus obtained can be reacted with, for example, anhydrous hydrogen fluoride, trifluoromethanesulfonic acid, or trifluoroacetic acid, in the presence of various additives to thereby achieve, in one step, separation of the peptide from the resin and removal of all protecting groups.

When a resin for synthesis of peptides with carboxyl-terminal carboxylic acid is used as the resin support, a peptide having a carboxyl group at the carboxyl terminus, for example, a peptide wherein $Y^1$ in the formula (II) is OH, can be obtained. When a resin for synthesis of peptides with carboxyl-terminal amide is used as the resin support, a peptide having amidated carboxylic acid at the carboxyl terminus, for example, a peptide wherein $Y^1$ in the formula (II) is $NH_2$, can be obtained.

The obtained peptide crude can be purified by peptide purification means known in the art. Examples thereof include gel filtration, column chromatography based on various principles (e.g., ion-exchange chromatography using a cation- or anion-exchange resin, hydrophobic chromatography, and partition/adsorption chromatography), and high-performance liquid chromatography.

When the peptide of the present invention comprises plural cysteine residues, these cysteine residues may be crosslinked. For example, $Cys^1$ and $Cys^2$ may be crosslinked in a 9-to 30-amino acid residue peptide, preferably 9- to 20-amino acid residue peptide, comprising an amino acid sequence represented by the following formula (IIIa):

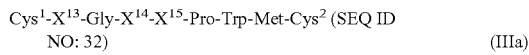

$Cys^1$-$X^{13}$-Gly-$X^{14}$-$X^{15}$-Pro-Trp-Met-$Cys^2$ (SEQ ID NO: 32)  (IIIa)

wherein $X^{13}$, $X^{14}$, and $X^{15}$ are the same or different and each represents an α-amino acid, and $Cys^1$ and $Cys^2$ may be crosslinked.

The crosslinking may be direct disulfide crosslinking between the cysteine residues or may be disulfide crosslinking via a disulfide compound used as a spacer. The disulfide crosslinking can be formed, for example, by oxidizing a dilute aqueous solution of a peptide with $K_3[Fe(CN)_6]$ or with iodine under acidic conditions.

The peptide of the present invention can be obtained in various salt forms. Examples of the salt include: salts with inorganic acids or with organic acids such as formic acid, acetic acid, tartaric acid, and citric acid; and salts with inorganic bases such as sodium and ammonium or with organic bases such as triethylamine, ethylamine, and methylamine.

The amino group of the peptide can be biotinylated, for example, by the usual HOBt-DCC or HBTu-HOBt method of condensing amino acid derivatives on a resin.

The screening method of the present invention is characterized by searching, from peptides having no proven activity of inhibiting amyloid β fibrillogenesis, a peptide which binds to a single-chain antibody having an activity of specifically binding to Aβ1-42 such that the fibrillogenesis reaction thereof is inhibited, and has an activity of inhibiting amyloid β fibrillogenesis.

Preferable examples of the single-chain antibody (scFv) having an activity of specifically binding to Aβ1-42 such that the fibrillogenesis reaction thereof is inhibited include human single-chain variant region fragments scFvs (B6, B7, D1, and F10) described in WO 2005/105998. In the present specification, these antibodies are referred to as templates.

The amino acid sequences of VH and VL chains of B6 scFv (clone B6 described in WO 2005/105998) are shown in SEQ ID NOs: 1 and 2, respectively.

The amino acid sequences of VH and VL chains of B7 scFv (clone B7 described in WO 2005/105998) are shown in SEQ ID NOs: 3 and 4, respectively.

The amino acid sequences of VH and VL chains of D1 scFv (clone D1 described in WO 2005/105998) are shown in SEQ ID NOs: 5 and 6, respectively.

The amino acid sequences of VH and VL chains of F10 scFv (clone F10 described in WO 2005/105998) are shown in SEQ ID NOs: 7 and 8, respectively.

Examples of a method for obtaining the peptide of the present invention include peptide library methods described below. The peptide library methods are further divided into a method using bacteriophages and a method of chemically synthesizing a library.

A phage random peptide library may be constructed by a method which involves ligating synthetic genes having a random sequence to, for example, genes encoding an M13 phage coat protein (e.g., gene III or VIII protein). The method described in, for example, Science, 249, 386 (1990) or Proc. Natl. Acad. Sci. USA, 87, 6378 (1990), can be used as this method. The sizes of the gene inserts are not particularly limited as long as peptides are stably expressed. Genes encoding 6 to 15 amino acids are preferable because the prepared library covers a larger number of random sequences and further has the ability to bind to the target molecule. To select a peptide phage that binds to scFv used as a template, the purified scFv is immobilized on a column or microtiter plate either directly or via anti-IgG antibodies or the like, and the library is brought into contact with the immobilized scFv. Then, unbound phages are washed away by washing operation. After washing, bound phages are eluted with an acid and neutralized. Then, E. coli is infected with the phages for amplification. This operation (panning) is repeated three or four times to thereby concentrate phages having affinity for the scFv. In this context, to obtain single clones, E. coli are infected with the phages again and incubated on an agar medium containing an antibiotic to form single colonies. Individual colonies are cultured in a liquid medium, and the phage in the supernatant is then concentrated by polyethylene glycol precipitation or the like. The nucleotide sequence thereof can be determined to thereby determine the peptide structure.

A peptide library having a random-amino acid sequence may also be prepared by chemical synthesis, in addition to the method using phage. Examples of a method thereof include a method using beads (Nature, 354, 82 (1991)), a liquid phase focusing method (Nature, 354, 84 (1991)), and a microplate method (Science, 251, 767 (1991)).

Examples of preparation of a large amount of a peptide that has the sequence obtained by the library include a method of artificially synthesizing peptides and a method of causing peptide expression in E. coli, yeast, insect cells, animal cells, etc., using a gene recombination technique.

The method of artificially synthesizing peptides can be performed easily according to a general peptide synthesis method and is performed conveniently by, for example, a solid-phase synthesis method. According to this method, mutants are also easily prepared by applying deletion, substitution, insertion, or addition to the sequence of interest (Cell Engineering (Saibo Kogaku in Japanese), suppl., Experimental Protocols for Anti-Peptide Antibodies, p. 26-46, Shujunsha Co., Ltd.). Moreover, modifications may also be performed, such as introduction of non-natural amino acids, chemical modification of each amino acid residue, or stabilization of a structure through intramolecular cyclization caused by introducing a cysteine residue.

When the gene recombination technique is used, a DNA sequence is determined from the obtained amino acid sequence according to codon usage (see Maniatis et al., Molecular Cloning, Appendix D1, Cold Spring Harbor Laboratory, 1989) and introduced into host cells according to an established technique. Furthermore, amino acids in the sequence may also be converted to other residues by introducing mutation into the nucleotide sequence. For example, for expression in E. coli, it is desired that the obtained DNA sequence should be linked to a promoter sequence, for example, a tryptophan synthase operon (Trp) or lactose operon (lac) promoter, and a ribosome-binding sequence, for example, a Shine-Dalgarno (SD) sequence, and a site that is recognized by a transcription termination factor should be added thereto. *E. coli* transformation with the prepared expression vector, etc., can be performed using the method described in Molecular Cloning (Maniatis et al., Cold Spring Harbor Laboratory, 1989). Expression products can be purified using, for example, various chromatography methods.

Examples of a method for examining whether or not the obtained peptide has an activity of inhibiting amyloid β fibrillogenesis include the thioflavine T (ThT) method (H. Levine, III, Protein Science 21: 404-410 (1993)).

The peptide confirmed to have an activity of inhibiting amyloid β fibrillogenesis according to the screening method of the present invention can be used as a lead compound. Deletion, substitution, insertion, or addition of one or two or more amino acid residues, or modifications can be applied thereto such that a peptide having an activity of inhibiting amyloid β fibrillogenesis is obtained to thereby produce a related amyloid β fibrillogenesis-inhibiting peptide. Whether or not this peptide has an activity of inhibiting amyloid β fibrillogenesis can be examined in the same way as in the method described above.

The present invention also provides an amyloid β fibrillogenesis-inhibiting peptide obtained by the screening method. In this context, the phrase "obtained by the screening method" means that the peptide has been confirmed to actually have the activity of inhibiting amyloid β fibrillogenesis by the screening method. The peptide has usually 6 to 40, preferably 8 to 20, more preferably 8 to 15 amino acid residues.

The peptide of the present invention has an activity of inhibiting amyloid β fibrillogenesis and is useful as a preventive or therapeutic agent for Alzheimer's disease.

The amyloid β fibrillogenesis-inhibiting peptide of the present invention can be administered orally or parenterally either directly or as a pharmaceutical composition comprising the peptide mixed with a pharmaceutically acceptable carrier, excipient, etc., known per se.

Specific examples of a dosage form for oral administration include tablets, pills, capsules, granules, fine granules, powders, syrups, emulsions, and suspension. Such dosage forms are produced according to a method known per se and contain carriers or excipients usually used in the pharmaceutical field. Examples of carriers or excipients for tablets include lactose, maltose, sucrose, starch, and magnesium stearate.

Examples of a dosage form for parenteral administration include eye drops, ointments, injections, poultices, suppositories, agents for nasal absorption, agents for pulmonary absorption, agents for transdermal absorption, and local sustained-release agents. Solution preparations can be prepared according to a method known per se in the art, for example, by dissolving the amyloid β fibrillogenesis-inhibiting peptide in a sterile aqueous solution usually used in injections, further emulsifying the mixture, and encapsulating the emulsion into liposomes. Peptides are susceptible to degradation by peptidase or the like in vivo and have the problem of accessibility to the site of interest, etc. Therefore, the appropriate delivery methods described herein, including liposomes, are preferably exploited in an embodiment of the present invention. The exploitation of such peptide delivery methods includes, but not limited to, the method using liposomes. Solid preparations can be prepared according to a method known per se in the art, for example, by adding an excipient such as mannitol, trehalose, sorbitol, lactose, or glucose to the amyloid β fibrillogenesis-inhibiting peptide and directly freeze-drying the mixture. Furthermore, this freeze-dried product can be powdered for use. Alternatively, these powders can be mixed with polylactic acid, glycolic acid, or the like and solidified for use. Gelling agents can be prepared according to a method known per se in the art, for example, by dissolving the amyloid β fibrillogenesis-inhibiting peptide in a thickener or polysaccharide such as glycerin, polyethylene glycol, methylcellulose, carboxymethylcellulose, hyaluronic acid, or chondroitin sulfate.

All of these preparations can be supplemented with a stabilizer such as human serum albumin, human immunoglobulin, $\alpha_2$ macroglobulin, or amino acids and can be supplemented with a dispersant or absorption promoter such as alcohol, sugar alcohol, or an ionic or non-ionic surfactant without impairing the activity of the amyloid β fibrillogenesis-inhibiting peptide. Moreover, a trace metal and an organic acid salt can also be added thereto, if necessary.

The dose of the pharmaceutical composition of the present invention is generally 0.001 to 1000 mg/kg of body weight per day for oral administration and 0.001 to 1000 mg/kg of body weight per day for intravenous, intramuscular, or subcutaneous administration, in terms of the peptide used as an active ingredient, although it differs depending on the activity of the peptide, the age and body weight of a patient, and the type or severity of disease. The number of doses is usually 1 to 3 doses per day for oral administration and 1 to 2 doses per day for injections.

BRIEF DESCRIPTION OF THE DRAWINGS

FIG. 5 is a diagram showing a list of peptide sequences displayed on phage clones isolated using, as a template, B6 scFv, B7 scFv, or D1 scFv that inhibits Aβ1-42 fibrillogenesis. The peptide sequences shown in FIG. 5 include pepB6-L1 (SEQ ID NO. 9); pepB6-L10 (SEQ ID NO. 10); pepD1-L5, L9 (SEQ ID NO. 11); pepD1-L6 (SEQ ID NO. 12); pepD1-L7 (SEQ ID NO. 13); pepD1-L13 (SEQ ID NO. 14); pepD1-L20 (SEQ ID NO. 15); pepB7-c15 (SEQ ID NO. 16); pepD1-c2, c13 (SEQ ID NO. 17); pepD1-c18 (SEQ ID NO. 18); pepD1-c3 (SEQ ID NO. 19); pepD1-c11 (SEQ ID NO. 20); pepD1-c5, C7, c20 (SEQ ID NO. 16); pepD1-c8 (SEQ ID NO. 21); and pepD1-c10 (SEQ ID NO. 22).

FIG. 6 is a diagram showing fusion molecules of a biotinylated B6 or B7scFv-binding sequence and a TAT sequence. The sequences shown in FIG. 6 include B6-L1 (SEQ ID NO. 9); B7-C15G (SEQ ID NO. 35); B7-S15 (SEQ ID NO. 23); TAT (SEQ ID NO. 30); TAT-B6-L1 (SEQ ID NO. 24); B6-L1-TAT (SEQ ID NO. 25); TAT-B7-C15 (SEQ ID NO. 26); and TAT-B7-S15 (SEQ ID NO. 27).

Figure 1:
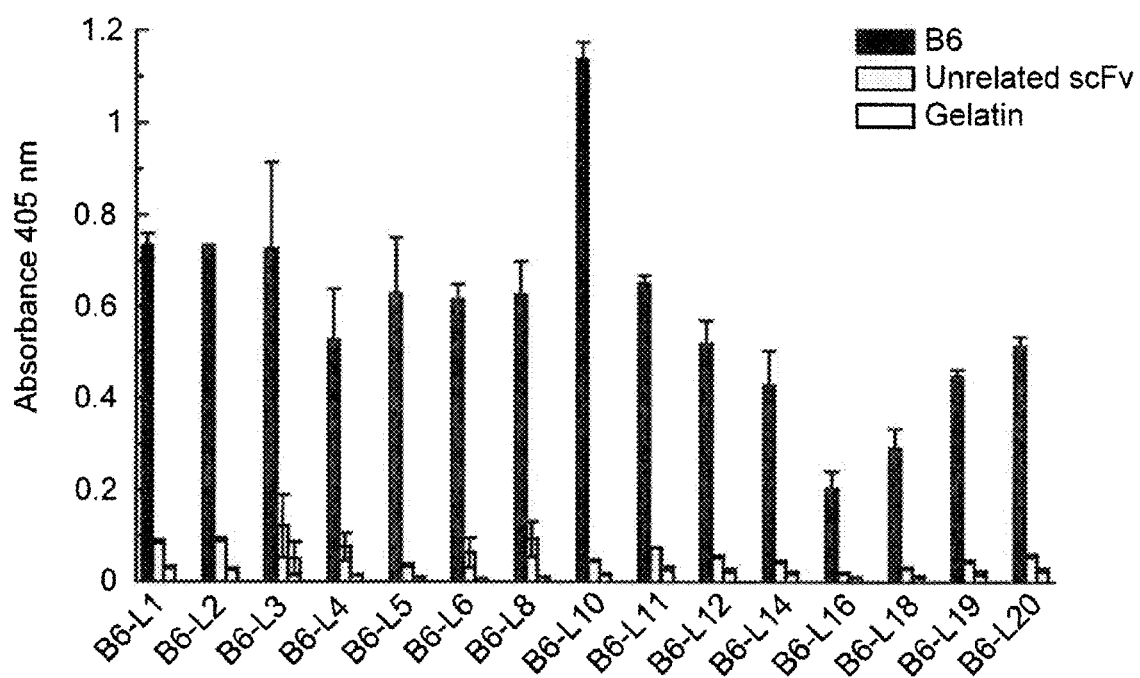
FIG. 1 is a diagram showing results of ELISA conducted on peptide phage clones bound to B6 scFv.

This description includes part or all of the contents as disclosed in the description and/or drawings of Japanese Patent Application No. 2006-125769, which is a priority document of the present application.

BEST MODE FOR CARRYING OUT THE INVENTION

Hereinafter, the present invention will be described more specifically with reference to Production Examples and Examples. However, the present invention is not intended to be limited to them.

Example 1

Experiments described below were conducted according to Kaji et al., J. Biochem. 129: 577-583 (2001) and S. Hashiguchi et al., J. Biochem. 133: 43-49 (2003).

1. Material and Method
(1) scFv Purification Using E-Tag Column

To express scFv binding to Aβ, E. coli strain HB2151 was infected with scFv phage clones according to the method of Hashiguchi et al. (J. Biochem. 133: 43-49 (2003)). From the obtained medium supernatant, amyloid-specific scFvs (B6, B7, D1, and F 10) were purified using an E-tag column (Amersham Biosciences).

(2) Peptide Phage Library

Peptide phage libraries used were Ph.D.-12 library (New England Biolabs, MA) which displays a 12-random amino acid sequence at the amino terminus of a phage gene III protein and Ph.D.-C7C library (New England Biolabs, MA) which displays a peptide containing a 7-amino acid sequence flanked by a pair of cysteine residues at the amino terminus of a phage gene III protein.

(3) Biopanning

A Maxisorp plate was coated with a human single-chain antibody (scFv: B6, B7, D1, or F10) used as a template or with control scFv in an amount of 1 μg/100 μl/well (0.1 M NaHCO$_3$, pH 8.6) at 4° C. for 6 hours. Each well was blocked with 0.5% gelatin for 1st panning, 0.25% BSA for 2nd panning, and 0.5% gelatin for 3rd panning as a blocking solution at 4° C. for 14 hours. The 12-mer or C7C peptide phage library was diluted ($1.5 \times 10^{12}$ pfu/100 μl) with a blocking solution and then left standing for 30 minutes. Then, absorption operation was performed using control scFv. Specifically, the well coated with control scFv was washed with 0.2% Tween 20/PBS (PBST) three times and reacted at room temperature for 1 hour by the addition of a phage solution. A phage solution that was not bound to control scFv was collected. The well coated with scFv used as a template was reacted at room temperature for 1 hour by the addition of the phage solution. Each well was washed with 0.2% PBST 10 times. After addition of 100 μl of 1 mg/ml BSA/0.1 M glycine hydrochloride, pH 2.2, the mixture was left at room temperature for 5 minutes to thereby collect bound phages. Immediately thereafter, the phages were neutralized by the addition of 15 μl of 1 M Tris-HCl, pH 9.1. E. coli ER2738 was infected with the collected phages for amplification. The amplified phages were used in the 2nd and 3rd rounds of panning ($1.5 \times 10^{12}$ pfu/100 μl).

(4) Isolation of Phage Clones

After two rounds of panning, ER2738 was infected with the collected phages and cultured on LB/Tet/X-gal plate. ER2738 was infected with the lysis of plaques again, and phage clones were isolated.

(5) ELISA

An ELISA plate was coated with scFv used as a template in the panning or with control scFv in an amount of 50 ng/40 μl/well (0.1 M NaHCO$_3$, pH 8.6) at 4° C. for 6 hours. Each well was blocked with 0.5% gelatin at 4° C. for 13 hours. Each well was washed with 0.2% PBST three times and then reacted at room temperature for 1 hour by the addition of the isolated peptide phage clone solution (approximately $1.6 \times 10^{11}$ virions/40 μl). After reaction with 40 μl of biotinylated anti-M13 monoclonal antibodies (diluted 1000 folds) and a streptavidin-alkaline phosphatase conjugate (diluted 1000 folds), bound phages were detected using substrate p-nitrophenyl phosphate.

(6) DNA sequencing

Phage clones confirmed to have specificity were treated with phenol/chloroform for protein removal. Then, DNA was purified by ethanol precipitation and used as a template in sequencing. A gene encoding the region having the random peptide sequence inserted therein was amplified using a primer-96gIII (1 pg/μl) 5'-CCC TCA TAG TTA GCG TAA CG-3' (SEQ ID NO: 33) (New England Biolabs, MA) and subjected to DNA sequencing.

(7) Peptide Synthesis

Peptides of the present invention were synthesized according to a general solid-phase peptide synthesis method, i.e., the Fmoc/fBTu+HOBt method. A TAT sequence was linked to each of the peptides B6-L1, B7-C15, and B7-S15 of the present invention to synthesize peptides. For the peptide B7-C15, glycine was added to the carboxyl terminus, and the TAT sequence was then linked to the resulting sequence. In this context, the TAT sequence is a peptide sequence having the function of passing through the blood-brain barrier (P. Jarver and Ulo Langel, The use of cell-penetrating peptides as a tool for gene regulation, DDT, 9: 395-401, 2004).

The B6-L1, B7-C15, and B7-S15 sequences having the TAT sequence fused at the amino terminus are referred to as TAT-B6-L1, TAT-B7-C15, and TAT-B7-S15, respectively. The B6-L1 sequence having the TAT sequence fused at the carboxyl terminus is referred to as B6-L1-TAT. To detect binding of the peptides, these peptide sequences were biotinylated at their amino termini for synthesis.

The amino acid sequences of B6-L1, B7-C15, and B7-S15 and their fusion molecules with the TAT sequence are represented by the following SEQ ID NOs:
B6-L1: SEQ ID NO: 9;
B7-C15: SEQ ID NO: 16;
B7-S15: SEQ ID NO: 23;
TAT-B6-L1: SEQ ID NO: 24;
B6-L1-TAT: SEQ ID NO: 25;
TAT-B7-C15: SEQ ID NO: 26; and
TAT-B7-S15: SEQ ID NO: 27.

(8) Experiment of Inhibition of Amyloid β Fibrillogenesis

The synthesized peptide (TAT-B6-L1, B6-L1-TAT, TAT-B7-C15, or TAT-B7-S15) was added at varying concentrations (1.65 nM, 16.5 nM, and 33 nM) to the Aβ1-42 peptide diluted to 40 M using 20 mM phosphate buffer, pH 7.0. At 0, 6, and 24 hours later, 101 of a sample was collected. After addition of 90 μl of 11 μM thioflavine T (Sigma)/phosphate buffer, fluorescence intensity at 482 nm generated by excitation light at 450 nm was measured using a multilabel plate counter Wallac 1420 ARVO sx (Perkin-Elmer; Wellesley, Mass.).

(9) Experiment of Precipitation of Aβ Conformers (Aβ Oligomer and Aβ Fibers) by Aβ Fibrillogenesis-Inhibiting Peptide Aβ1-42 was dissolved at a concentration of 40 μM in 20 mM phosphate buffer, pH 7.0. At 1.5 hours later, the solution was reacted at 37° C. for 1 hour by the addition of the TAT-B6-L1 or TAT-B7-C15 peptide adjusted to 40 μM at a ratio of 1:1 by liquid volume (final concentration: Aβ [20 μM]/synthesized peptide [20 μM]). After reaction, an aliquot thereof was sampled as a sample before immunoprecipitation ("Before precipitation"), and the remaining sample was reacted with M-280 streptavidin-magnet beads (Dynal Biotech, Oslo, Norway) adjusted to 20 µg/µl on ice for 1 hour at a ratio of 1:1 by liquid volume (final concentration: Aβ [10 µM]/synthesized peptide [10 µM]/beads [10 µg/µl]). After reaction, the beads were precipitated using a magnet to obtain "Supernatant". To the precipitated beads, PBS was added in a liquid volume equal to the collected supernatant to obtain "Pellet". Each obtained sample was electrophoresed and subjected to Western blot analysis using anti-Aβ antibodies.

2. Results (1) Peptide Phage Clones that Bind to Aβ-Specific scFv (a) Results of ELISA conducted on peptide phage clones bound to B6 scFv are shown in FIG. 1. Fv1E1, an antibody that does not inhibit Aβ fibrillogenesis, was used as unrelated scFv (control scFv). A phage library used was Ph.D.-12 library (New England Biolabs, MA) which displays a 12-mer amino acid sequence. The experiment was conducted according to the procedures described in the paragraph (5) ELISA.

Figure 2:
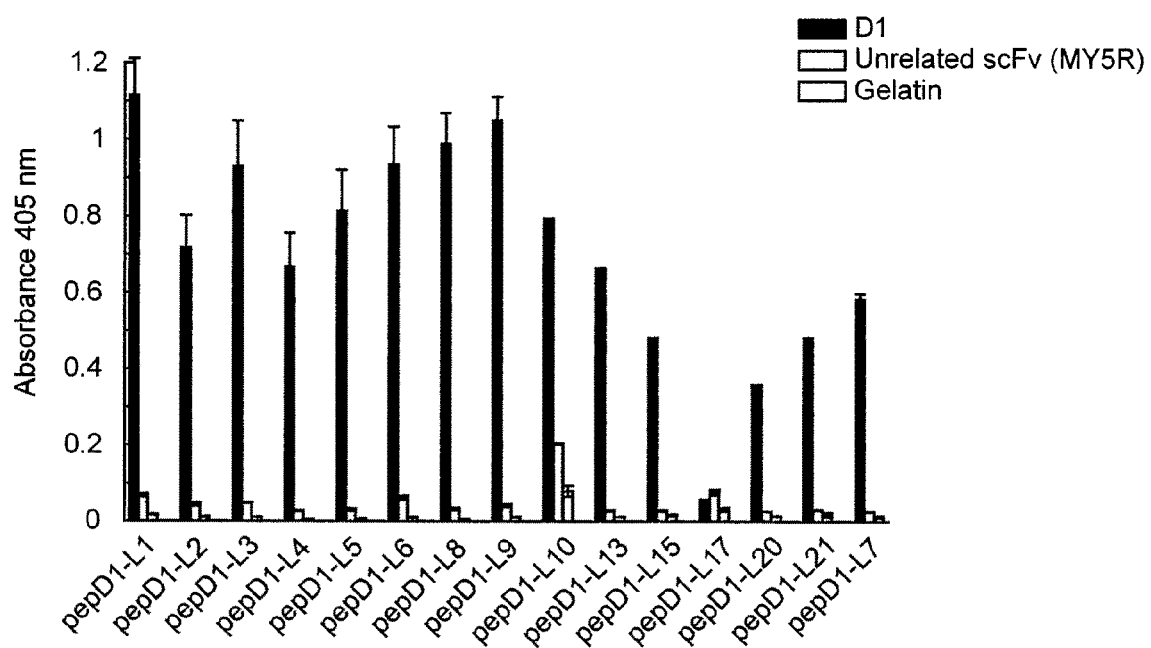
FIG. 2 is a diagram showing results of ELISA conducted on 12-mer peptide phage clones bound to D1 scFv.

(b) Results of ELISA conducted on 12-mer peptide phage clones bound to D1 scFv are shown in FIG. 2. MY5R, an antibody that does not inhibit Aβ fibrillogenesis, was used as unrelated scFv (control scFv). A phage library used was Ph.D.-12 library (New England Biolabs, MA) which displays a 12-mer amino acid sequence. The experiment was conducted according to the procedures described in the paragraph (5) ELISA.

Figure 3:
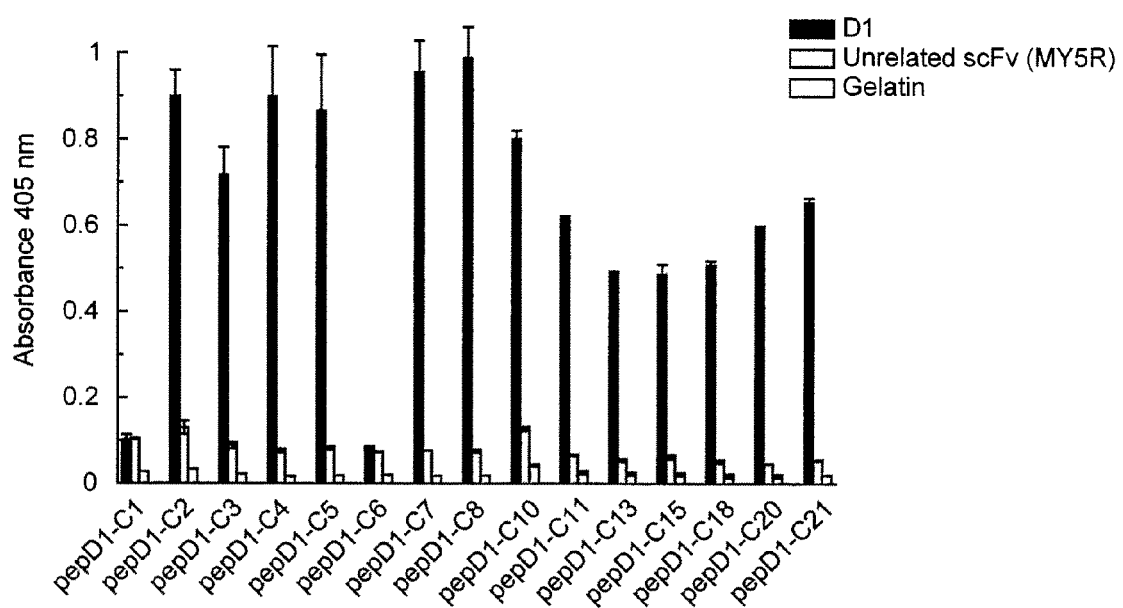
FIG. 3 is a diagram showing results of ELISA conducted on C7C peptide phage clones bound to D1 scFv.

(c) Results of ELISA conducted on C7C peptide phage clones bound to D1 scFv are shown in FIG. 3. MY5R, an antibody that does not inhibit Aβ fibrillogenesis, was used as unrelated scFv (control scFv). A phage library used was Ph.D.-C7C library (New England Biolabs, MA) which displays a peptide containing a 7-amino acid sequence flanked by a pair of cysteine residues. The experiment was conducted according to the procedures described in the paragraph (5) ELISA.

(2) Activity of Inhibiting Aβ1-42 Fibrillogenesis by B6-Binding Peptide Phages

Figure 4:
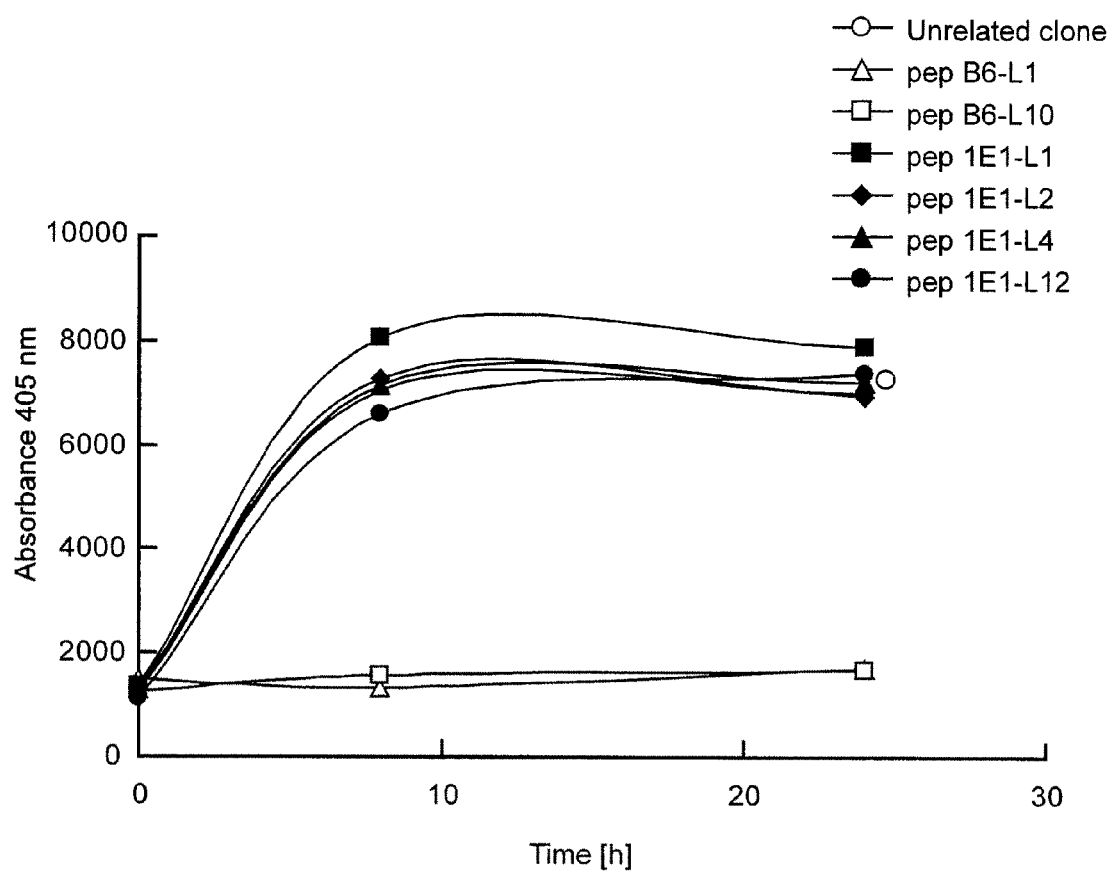
FIG. 4 is a diagram showing results of an experiment of inhibition of Aβ1-42 peptide fibrillogenesis by peptide phages.

Results of an experiment of inhibition of Aβ1-42 peptide fibrillogenesis by B6-binding peptide phages are shown in FIG. 4. The experiment of inhibition of Aβ1-42 fibrillogenesis was conducted according to the procedures described in the paragraph (8) Experiment of inhibition of fibrillogenesis. pepB6-L1 and pepB6-L10 are phage clones isolated using, as a template, B6 scFv that inhibits Aβ1-42 fibrillogenesis, and these phage clones bind thereto. pep1E1-L1, pep1E1-L2, pep1E1-L4, and pep1E1-L12 are phage clones isolated using, as a template, Fv1E1 scFv (described in the paragraphs [0074] to [0075] in WO 2005-105998) that does not inhibit Aβ1-42 fibrillogenesis. The concentrations of the phage clones used here are $3.0 \times 10^{12}$ virions/ml.

(3) Aβ-Specific scFv Epitope (Binding Sequence)

A list of amino acid sequences of peptides displayed on phage clones isolated using, as a template, B6 scFv, B7 scFv, or D1 scFv that inhibits Aβ1-42 fibrillogenesis is shown in FIG. 5. A phage library used was Ph.D.-12 library (in FIG. 5, abbreviated to 12-mer*) or Ph.D.-C7C library (in FIG. 5, abbreviated to C7C*). pepB7-C15 and pepD1-C5, C7, C20 have the same sequence. L and C indicated before the number represent clones isolated from the 12-mer and C7C libraries, respectively.

The amino acid sequence of a peptide displayed on each phage clone is represented by the following SEQ ID NOs:
pepB6-L1: SEQ ID NO: 9;
pepB6-L10: SEQ ID NO: 10;
pepD1-L5, L9: SEQ ID NO: 11;
pepD1-L6: SEQ ID NO: 12;
pepD1-L7: SEQ ID NO: 13;
pepD1-L13: SEQ ID NO: 14;
pepD1-L20: SEQ ID NO: 15;
pepB7-C15 (pepD1-C5, C7, C20): SEQ ID NO: 16;
pepD1-C2, C13: SEQ ID NO: 17;
pepD1-C18: SEQ ID NO: 18;
pepD1-C3: SEQ ID NO: 19;
pepD1-C11: SEQ ID NO: 20;
pepD1-C8: SEQ ID NO: 21; and
pepD1-C10: SEQ ID NO: 22.

(4) Fusion Molecule of Biotinylated B6 or B7 scFv-Binding Sequence and Tat Sequence A fusion molecule of a biotinylated B6 scFv-binding sequence and a TAT sequence is shown in FIG. 6. The B6-L1, B7-C15, and B7-S15 sequences having the TAT sequence fused at the amino terminus are referred to as TAT-B6-L1, TAT-B7-C15, and TAT-B7-S15, respectively. The B6-L1 sequence having the TAT sequence fused at the carboxyl terminus is referred to as B6-L1-TAT. The TAT sequence is a peptide sequence having the function of passing through the blood-brain barrier (P. Jarver and Ulo Langel, The use of cell-penetrating peptides as a tool for gene regulation, DDT, 9: 395-402, 2004). These peptides were biotinylated at their amino termini. Binding of the peptides was quantified using avidin labeled with an enzyme.

Figure 7:
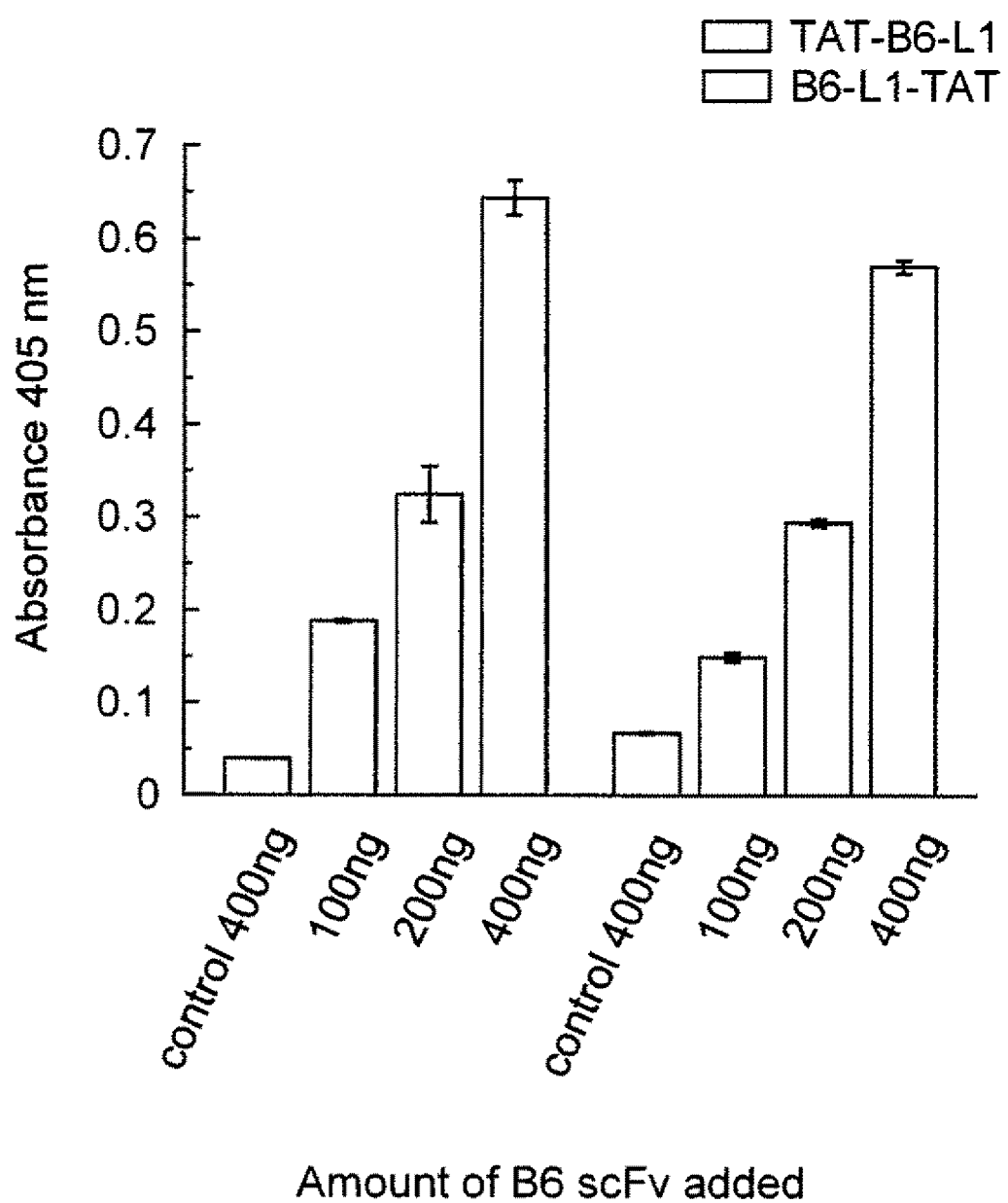
FIG. 7 is a diagram showing that a fusion peptide of TAT and B6-L1 is recognized by B6 scFv.

(5) The fusion peptide of TAT and B6-L1 was recognized by B6 scFv (FIG. 7). An ELISA plate was coated with the synthesized peptide TAT-B6-L1 or B6-L1-TAT under conditions of 200 ng/well. After addition of B6 scFv at varying concentrations, its binding activity was studied. A control peptide used was an unrelated peptide (GSGGGSCGY-WRSEWGLCG (SEQ ID NO: 34). Binding reaction dependent on the amount of B6 scFv was confirmed.

(6) Activity of Inhibiting Aβ1-42 Fibrillogenesis by Fusion Peptide of Tat and B6-L1, B7-C15, or B7-S15

Figure 8:
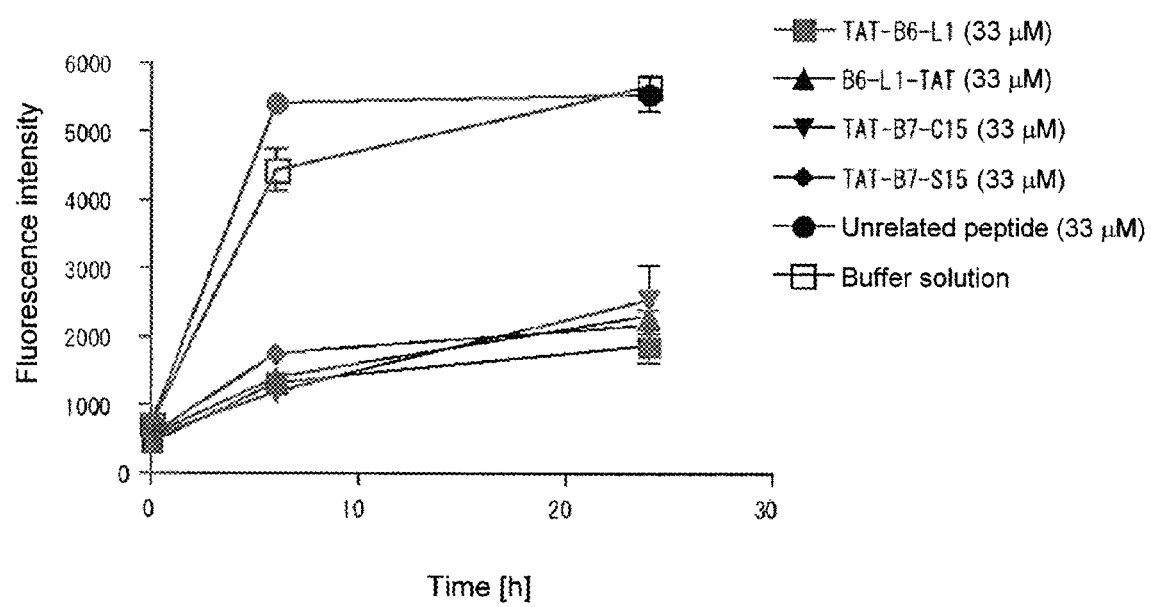
FIG. 8 is a diagram showing results of measuring an activity of inhibiting Aβ1-42 fibrillogenesis by a fusion peptide of TAT and B6-L1, B7-C15, or B7-S15.

Results of measuring an activity of inhibiting Aβ1-42 fibrillogenesis by fusion peptides of TAT and B6-L1, B7-C15, or B7-S15 are shown in FIG. 8. The experiment of inhibition of fibrillogenesis was conducted according to the procedures described in the experiment of inhibition of fibrillogenesis above. TAT-B6-L1, B6-L1-TAT, TAT-B7-C15, and TAT-B7-S15 were demonstrated to have the activity of inhibiting fibrillogenesis. The control peptide exhibited no inhibiting activity.

Figure 9:
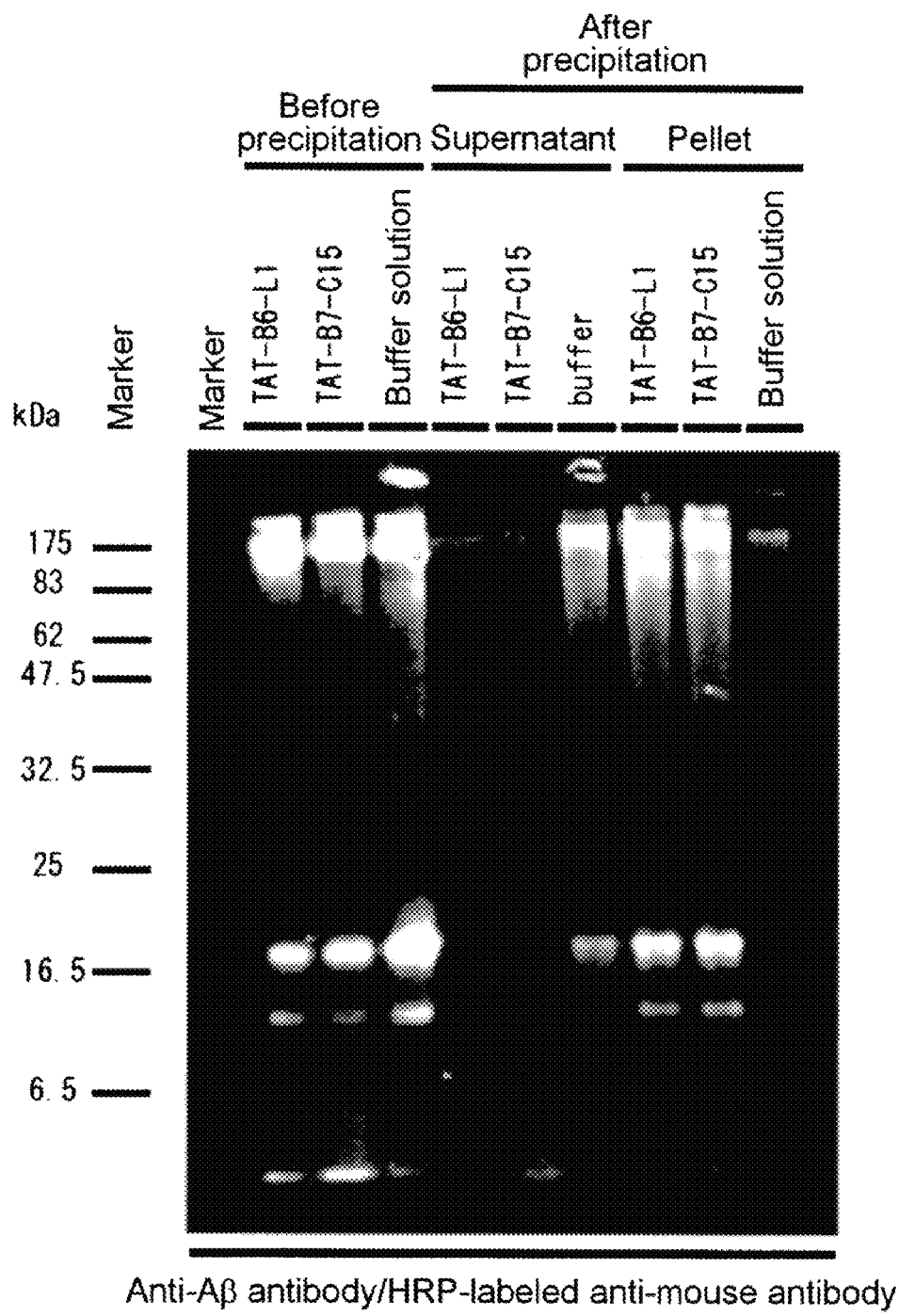
FIG. 9 is a diagram showing results of an experiment of precipitation of Aβ conformers (Aβ oligomer and Aβ fibers) by a fusion peptide of TAT and B6-L1 or B7-C15.

(7) Experiment of Precipitation of Aβ Conformers (Aβ Oligomer and Aβ Fibers) by TAT-B6-L1 or TAT-B7-C15 Peptide Results of an experiment of precipitation of the TAT-B6-L1 or TAT-B7-C15 peptide are shown in FIG. 9. Aβ1-42 was dissolved at a concentration of 40 µM in 20 mM phosphate buffer, pH 7.0. At 1.5 hours later, the biotinylated TAT-B6-L1 or TAT-B7-C15 peptide was added thereto, and the conjugates were precipitated using streptavidin-magnet beads. Bands derived from Aβ oligomer, Aβ fibers, etc., could be confirmed before precipitation. Aβ oligomer or Aβ fibers were not confirmed in the supernatant from precipitation using the TAT-B6-L1 or TAT-B7-C15 peptide but could be confirmed in the pellet. These results demonstrated that Aβ oligomer or Aβ fibers formed on 1.5 hours after dissolution of Aβ1-42 bind to the TAT-B6-L1 or TAT-B7-C15 peptide. The unrelated control peptide had no confirmed precipitation reaction (not shown in FIG. 9).

All publications, patents, and patent applications cited herein are incorporated herein by reference in their entirety.

INDUSTRIAL APPLICABILITY

A peptide of the present invention is useful as a preventive or therapeutic agent for Alzheimer's disease.

The invention claimed is:

1. A 9- to 30-amino acid residue peptide comprising an amino acid sequence represented by the following formula (III):

$$Z^1\text{-}X^{13}\text{-}Gly\text{-}X^{14}\text{-}X^{15}\text{-}Pro\text{-}Trp\text{-}Met\text{-}Z^2 \text{ (SEQ ID NO: 31)} \quad \text{(III)}$$

wherein $X^{13}$ is an aromatic amino acid, $X^{14}$ is a hydroxyamino acid, and $X^{15}$ is a basic amino acid and, $Z^1$ and $Z^2$ are the same or different and each represents cysteine or serine, and when $Z^1$ and $Z^2$ represent cysteine, they may be crosslinked.

2. The peptide according to claim 1, wherein the peptide is a 20- to 30-amino acid residue peptide comprising the amino acid sequence represented by the formula (III) and a TAT sequence represented by the following formula:

Tyr-Gly-Arg-Lys-Lys-Arg-Arg-Gln-Arg-Arg-Arg (SEQ ID NO: 30).

3. A composition comprising the peptide according to claim 2 mixed with a carrier or excipient.

4. A method for reducing amyloid β 1-42 fibrillogenesis comprising administering an effective amount of the peptide according to claim 2 to a subject in need thereof.

5. The peptide according to claim 1, wherein the peptide is represented by SEQ ID No. 16, SEQ ID No. 23, SEQ ID No. 26, SEQ ID No. 27, or SEQ ID No. 35.

6. The peptide according to claim 1, wherein $Z^1$ and $Z^2$ are cysteine, and wherein $Z^1$ and $Z^2$ are crosslinked.

7. The peptide according to claim 1, wherein $X^{13}$ is phenylalanine or tyrosine, $X^{14}$ is serine or threonine, and $X^{15}$ is lysine, hydroxylysine, or arginine.

* * * * *

SEQUENCE LISTING

<160> NUMBER OF SEQ ID NOS: 35

<210> SEQ ID NO 1
<211> LENGTH: 123
<212> TYPE: PRT
<213> ORGANISM: Homo sapiens

<400> SEQUENCE: 1

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Met Ser Gly Ser Gly Asp Thr Thr Tyr Tyr Ala Asp Ser Val
    50                  55                  60

Lys Gly Arg Phe Thr Ile Ser Arg Asp Asn Ser Lys Lys Thr Val Tyr
65                  70                  75                  80

Leu Gln Met Asn Arg Leu Arg Val Glu Asp Thr Ala Ile Tyr Tyr Cys
                85                  90                  95

Ala Lys Asp Gly Arg Phe Arg Asn Arg Arg Ser Asp Gly Phe Asp Thr
            100                 105                 110

Trp Gly Gln Gly Thr Leu Val Thr Val Ser Ser
        115                 120

<210> SEQ ID NO 2
<211> LENGTH: 109
<212> TYPE: PRT
<213> ORGANISM: Homo sapiens

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asp Asn Arg Pro Ser Gly Ile Pro Asp Arg Phe Ser Gly Ser
    50                  55                  60

Ser Ser Gly Asn Ala Ala Ser Leu Thr Ile Thr Gly Ala Gln Ala Glu
65                  70                  75                  80

Asp Glu Ala Asp Tyr Tyr Cys Asn Ser Arg Asp Thr Ser Gly Asn His
                85                  90                  95

Leu Val Phe Gly Gly Gly Thr Lys Val Thr Val Leu Gly
            100                 105

<210> SEQ ID NO 3
<211> LENGTH: 123
<212> TYPE: PRT
<213> ORGANISM: Homo sapiens

<400> SEQUENCE: 3

Gln Val Gln Leu Val Gln Ser Gly Gly Gly Leu Val Gln Pro Gly Gly
1               5                   10                  15

Ser Gln Arg Leu Ser Cys Ala Ala Ser Gly Phe Gly Phe Ser Asn Tyr
            20                  25                  30

Ala Val Ser Trp Val Arg Gln Ala Pro Gly Thr Gly Leu Glu Trp Val

```
                35                  40                  45
Ala Gly Val Asn Gly Gly Gln Asn Thr Phe Tyr Ala Asp Ser Val
 50                  55                  60
Lys Gly Arg Phe Thr Ile Ser Arg Asp Asn Ser Lys Lys Thr Val Tyr
 65                  70                  75                  80
Leu Gln Met Asn Ser Leu Arg Val Glu Asp Thr Ala Ile Tyr Tyr Cys
                 85                  90                  95
Ala Lys Asp Gly Arg Phe Arg Asn Arg Pro Asp Gly Phe Asp Thr
            100                 105                 110
Trp Gly Gln Gly Thr Leu Val Thr Val Ser Ser
            115                 120

<210> SEQ ID NO 4
<211> LENGTH: 109
<212> TYPE: PRT
<213> ORGANISM: Homo sapiens

<400> SEQUENCE: 4

Ser Ser Glu Leu Thr Gln Asp Pro Asn Val Ser Val Ala Leu Gly Gln
 1               5                  10                  15
Thr Val Arg Ile Thr Cys Gln Gly Asp Thr Leu Arg Asn Asn Phe Pro
                20                  25                  30
Thr Trp Tyr Gln Gln Lys Pro Gly Gln Ala Pro Val Leu Val Phe Tyr
             35                  40                  45
Gly Lys Asp Asn Arg Pro Ser Gly Ile Pro Asp Arg Phe Ser Gly Ser
 50                  55                  60
Arg Ser Gly Thr Thr Ala Ser Leu Val Ile Thr Gly Ala Gln Ala Gln
 65                  70                  75                  80
Asp Glu Ala Asp Tyr Tyr Cys Asn Ser Arg Asp Ser Gly Gly His His
                 85                  90                  95
Leu Val Phe Gly Gly Gly Thr Lys Leu Thr Val Leu Gly
            100                 105

<210> SEQ ID NO 5
<211> LENGTH: 117
<212> TYPE: PRT
<213> ORGANISM: Homo sapiens

<400> SEQUENCE: 5

Gln Val Thr Leu Lys Glu Ser Gly Gly Asp Leu Val Lys Pro Gly Gly
 1               5                  10                  15
Ser Leu Arg Leu Ser Cys Ala Ala Ser Gly Phe Thr Phe Arg Lys Tyr
                20                  25                  30
Tyr Met Ala Trp Ile Arg Gln Ala Pro Gly Lys Gly Pro Glu Trp Leu
             35                  40                  45
Ser Thr Ile Ser Asn Ser Gly Asp Ile Ile Asp Tyr Ala Asp Ser Val
 50                  55                  60
Arg Gly Arg Phe Ser Ile Ser Arg Asp Asn Ala Gln Lys Ser Leu Tyr
 65                  70                  75                  80
Leu Gln Met Thr Ser Leu Arg Pro Asp Asp Ser Ala Ile Tyr Tyr Cys
                 85                  90                  95
Ala Arg Glu Tyr Phe Phe Ser Phe Asp Val Trp Gly Arg Gly Thr Leu
            100                 105                 110
Val Thr Val Ser Ser
            115

<210> SEQ ID NO 6
```

```
<211> LENGTH: 109
<212> TYPE: PRT
<213> ORGANISM: Homo sapiens

<400> SEQUENCE: 6

Ser Ser Glu Leu Thr Gln Asp Pro Ala Val Ser Val Ala Leu Gly Gln
1               5                   10                  15

Thr Ile Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Lys Arg Pro Ser Gly Ile Pro Asp Arg Ile Ser Gly Ser
        50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Gln Leu Thr Val Leu Gly
            100                 105

<210> SEQ ID NO 7
<211> LENGTH: 125
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Arg Phe Ala Ala Ala Arg Arg Gly Leu Asp Ala Phe
            100                 105                 110

Asp Ile Trp Gly Gln Gly Thr Met Val Thr Val Ser Ser
        115                 120                 125

<210> SEQ ID NO 8
<211> LENGTH: 109
<212> TYPE: PRT
<213> ORGANISM: Homo sapiens

<400> SEQUENCE: 8

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
```

```
                65                  70                  75                  80
Asp Glu Ala Asp Tyr Tyr Cys Asn Ser Arg Asp Ser Ser Gly Asn His
                    85                  90                  95

Leu Val Phe Gly Gly Gly Thr Lys Leu Thr Val Leu Gly
            100                 105
```

```
<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 9

Gly Met Leu Asp Ile Phe Ala Pro Ile Arg His Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 10

Thr Ser Pro Ile Leu Asp Val Leu Thr Pro Pro Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 11

Gly Ser Pro Phe Leu Asp Leu Leu Ala Pro Ala Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 12

Ser Ser Ile Ile Asp Ile Leu Leu Pro Pro Ile Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 13
```

```
Ser Ile Leu Asp Ile Leu Ser Pro Arg Leu Ala Glu
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 14

```
Gly Asn Thr Leu Leu Asp Thr Leu Val Pro Leu Ile
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 15

```
Asn Pro Leu Asp Phe Tyr Ala Pro Ser Ile Leu Pro
1               5                   10
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 16

```
Cys Tyr Gly Thr Lys Pro Trp Met Cys
1               5
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 17

```
Cys Tyr Gly Thr Glu Pro Trp Met Cys
1               5
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 18

```
Cys Phe Gly His Glu Pro Trp Met Cys
1               5
```

<210> SEQ ID NO 19

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 19

Cys Gln Gly His Leu Pro Trp Met Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 20

Cys Phe Gly His Lys Pro Trp Met Cys
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 21

Cys Phe Gly Arg Leu Pro Trp Met Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 22

Cys Phe Gly Ser Leu Pro Trp Met Cys
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide based on the DNA sequence of phage
      binding to human antiamyloid beta peptide antibody

<400> SEQUENCE: 23

Ser Tyr Gly Thr Lys Pro Trp Met Ser Gly
1               5                   10

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide based on the DNA sequence of phage
    binding to human antiamyloid beta peptide antibody

<400> SEQUENCE: 24

Tyr Gly Arg Lys Lys Arg Arg Gln Arg Arg Gly Met Leu Asp Ile
1               5                   10                  15

Phe Ala Pro Ile Arg His Val
            20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
    peptide based on the DNA sequence of phage
    binding to human antiamyloid beta peptide antibody

<400> SEQUENCE: 25

Gly Met Leu Asp Ile Phe Ala Pro Ile Arg His Val Tyr Gly Arg Lys
1               5                   10                  15

Lys Arg Arg Gln Arg Arg Arg
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide based on the DNA sequence of phage
    binding to human antiamyloid beta peptide antibody

<400> SEQUENCE: 26

Tyr Gly Arg Lys Lys Arg Arg Gln Arg Arg Cys Tyr Gly Thr Lys
1               5                   10                  15

Pro Trp Met Cys Gly
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide based on the DNA sequence of phage
    binding to human antiamyloid beta peptide antibody

<400> SEQUENCE: 27

Tyr Gly Arg Lys Lys Arg Arg Gln Arg Arg Ser Tyr Gly Thr Lys
1               5                   10                  15

Pro Trp Met Ser Gly
            20

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: Any branched chain amino acid
<220> FEATURE:
<221> NAME/KEY: MOD_RES
<222> LOCATION: (3)..(5)

```
<223> OTHER INFORMATION: Any alpha-amino acid
<220> FEATURE:
<221> NAME/KEY: MOD_RES
<222> LOCATION: (7)..(8)
<223> OTHER INFORMATION: Any alpha-amino acid
<220> FEATURE:
<223> OTHER INFORMATION: see specification as filed for detailed
      description of substitutions and preferred embodiments

<400> SEQUENCE: 28

Xaa Asp Xaa Xaa Xaa Pro Xaa Xaa
1               5

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any alpha-amino acid or not present
<220> FEATURE:
<221> NAME/KEY: MOD_RES
<222> LOCATION: (5)..(5)
<223> OTHER INFORMATION: Any branched chain amino acid
<220> FEATURE:
<221> NAME/KEY: MOD_RES
<222> LOCATION: (7)..(9)
<223> OTHER INFORMATION: Any alpha-amino acid
<220> FEATURE:
<221> NAME/KEY: MOD_RES
<222> LOCATION: (11)..(12)
<223> OTHER INFORMATION: Any alpha-amino acid
<220> FEATURE:
<221> NAME/KEY: MOD_RES
<222> LOCATION: (13)..(14)
<223> OTHER INFORMATION: Any alpha-amino acid or not present
<220> FEATURE:
<223> OTHER INFORMATION: C-term OH or NH2
<220> FEATURE:
<223> OTHER INFORMATION: see specification as filed for detailed
      description of substitutions and preferred embodiments

<400> SEQUENCE: 29

Xaa Xaa Xaa Xaa Xaa Asp Xaa Xaa Xaa Pro Xaa Xaa Xaa Xaa
1               5                   10

<210> SEQ ID NO 30
<211> LENGTH: 11
<212> TYPE: PRT
<213> ORGANISM: Unknown
<220> FEATURE:
<223> OTHER INFORMATION: Description of Unknown: TAT peptide

<400> SEQUENCE: 30

Tyr Gly Arg Lys Lys Arg Arg Gln Arg Arg
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or Ser
<220> FEATURE:
<221> NAME/KEY: MOD_RES
```

```
<222> LOCATION: (2)..(2)
<223> OTHER INFORMATION: Any alpha-amino acid
<220> FEATURE:
<221> NAME/KEY: MOD_RES
<222> LOCATION: (4)..(5)
<223> OTHER INFORMATION: Any alpha-amino acid
<220> FEATURE:
<221> NAME/KEY: MOD_RES
<222> LOCATION: (9)..(9)
<223> OTHER INFORMATION: Cys or Ser
<220> FEATURE:
<223> OTHER INFORMATION: see specification as filed for detailed
      description of substitutions and preferred embodiments

<400> SEQUENCE: 31

Xaa Xaa Gly Xaa Xaa Pro Trp Met Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any alpha-amino acid
<220> FEATURE:
<221> NAME/KEY: MOD_RES
<222> LOCATION: (4)..(5)
<223> OTHER INFORMATION: Any alpha-amino acid
<220> FEATURE:
<223> OTHER INFORMATION: see specification as filed for detailed
      description of substitutions and preferred embodiments

<400> SEQUENCE: 32

Cys Xaa Gly Xaa Xaa Pro Trp Met Cys
1               5

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccctcatagt tagcgtaacg                                               20

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ser Gly Gly Gly Ser Cys Gly Tyr Trp Arg Ser Glu Trp Gly Leu
1               5                   10                  15

Cys Gly

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                peptide

<400> SEQUENCE: 35

Cys Tyr Gly Thr Lys Pro Trp Met Cys Gly
1               5                   10
```